US006670122B2

(12) United States Patent
Rosenow et al.

(10) Patent No.: US 6,670,122 B2
(45) Date of Patent: Dec. 30, 2003

(54) METHOD FOR DETECTING TRANSCRIPTION TEMPLATES

(75) Inventors: Carsten Rosenow, Mountain View, CA (US); Rini Saxena, Mountain View, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 09/683,221

(22) Filed: Dec. 3, 2001

(65) Prior Publication Data

US 2003/0104367 A1 Jun. 5, 2003

(51) Int. Cl.⁷ .............. C12Q 1/68; C12P 19/34; C07H 21/02
(52) U.S. Cl. .............. 435/6; 435/91.1; 435/91.2; 536/24.3
(58) Field of Search .............. 435/6, 91.1, 91.2; 536/24.3

(56) References Cited

U.S. PATENT DOCUMENTS 4,943,531 A * 7/1990 Goff et al. .................. 435/194
6,040,138 A * 3/2000 Lockhart et al. .............. 435/6
6,370,478 B1 * 4/2002 Stoughton et al. ............ 702/19

OTHER PUBLICATIONS

Stratagene Catalog p. 39, 1988.*
De MArtynoff et al. Archives Internationale de Physiologie et de Biochimie 1980, 88(2) B76–B77. Abstract only.*

* cited by examiner

*Primary Examiner*—Jezia Riley
(74) *Attorney, Agent, or Firm*—Wei Zhou

(57) ABSTRACT

Methods are provided for detecting the sense and antisense transcripts and for determining template strand of a genomic DNA. Exemplary methods include reverse transcribing transcripts without second strand synthesis. The resulting single stranded DNA is labeled and detected using nucleic acid probe arrays. In a particularly embodiment, actinomycin is used to inhibit the synthesis of second strand cDNA during reverse transcription.

25 Claims, 2 Drawing Sheets

METHOD FOR DETECTING TRANSCRIPTION TEMPLATES

BACKGROUND OF THE INVENTION

The present invention is in the field of genetic analysis for medical diagnosis, genetic variation research, or genetic engineering. More specifically, the present invention is in the field of nucleic acid analysis.

For many studies involving microarrays, labeled cDNA is often used as a target. This cDNA can be synthesized through either oligo d(T) primers which bind to the poly (A) tail in eukaryotic mRNA or through random primers, in which the actual binding sequences are not known. It is known that during in vitro reverse transcription of RNA, not only the first-strand cDNA is synthesized but also the second-strand cDNA, as reverse transcriptase can use either RNA or DNA as a template (see, e.g., Gubler, 1987. Second-strand cDNA synthesis: classical method. Methods Enzymol. 152:325–9; Gubler, 1987. Second-strand cDNA synthesis: mRNA fragments as primers. Methods Enzymol. 152:330–5; Kim et al., 1996. Human immunodeficiency virus reverse transcriptase. Functional mutants obtained by random mutagenesis coupled with genetic selection in *Escherichia coli*. J Biol Chem. 271(9):4872–8; Krug, M. S., and S. L. Berger, 1987. First-strand cDNA synthesis primed with oligo(dT). Methods Enzymol. 152:316–25). There may be many mechanisms by which this second-strand priming occurs. Two possible mechanisms have been studied, either the second strand cDNA is synthesized through re-priming of random hexamers with first strand cDNA or through the hairpin loop formation at the 5" end of first-strand cDNA.

High-density oligonucleotides have been widely used for gene expression analysis. In addition, it is an ideal platform for other applications like transcriptome analysis, antisense detection, splice variant detection, genotyping, etc. Some of these applications use random hexamer cDNA synthesis for target preparation. The synthesis of second strand cDNA would make the data analysis complicated due to the additional strand synthesis (e.g., antisense RNA could not be identified). Therefore, there is a need in the art for methods that can uniquely identify the sense strand. In addition, methods for identifying the template strand of a genomic DNA are needed.

SUMMARY OF THE INVENTION

In one aspect of the invention, methods are provided for detecting a plurality of transcripts without the interference of second strand DNA. The methods include synthesizing a plurality of cDNAs complementary with the transcripts by reverse transcription; where the synthesis of second strand cDNA is inhibited; and hybridizing the cDNAs or nucleic acids derived from the cDNAs with a nucleic acid probe array to detect and identify the transcripts. The methods are particularly suitable for detecting a large number of, at least 100, 1000, or 10000, transcripts. Any suitable second strand cDNA synthesis inhibition methods are suitable for use with at least some embodiments of the invention. In particularly preferred embodiments, hairpin loop formation inhibition is used to inhibit second strand cDNA synthesis. In one particularly preferred embodiment, the synthesis of the second strand cDNA is inhibited by the presence of actinomycin D, DMSO or sodium pyrophosphate. The cDNAs or nucleic acids derived from the cDNAs (e.g., products of PCR amplification of the cDNAs, etc.) may be labeled with any suitable labels, such as radioactive labels, fluorescent labels, and chemoluminescent labels, etc.

The nucleic acid array can be a high density oligonucleotide probe array with at least 400, 1000, 10000 probes per $cm^2$. In preferred embodiments, the array contains at least one probe against a target sequence and one probe against the reverse complementary sequence of the target sequence. In more preferred embodiments, the array contains at least 100 probes against at least 100 target sequences and at least 100 probes against at least 100 reverse complementary sequences of the target sequences. In even more preferred embodiments, the array comprises at least 1000 or 3000 probes against at least 1000 or 3000 target sequences and at least 1000 or 3000 probes against at least 1000 or 3000 reverse complementary sequences of the target sequences.

In another aspect of the invention, methods are provided for detecting the transcribed regions of a genome and the template strand of the genomic DNA. The methods are particularly suitable for analyzing regions where both strands of the genomic DNA may be transcribed. In preferred embodiments, the methods include obtaining a sample containing transcripts transcribed from the genome; synthesizing single stranded cDNAs complementary with the transcripts, where the synthesis of second strand cDNA is inhibited; and hybridizing the cDNAs or nucleic acids derived from the cDNAs with a nucleic acid probe array, where the nucleic acid probe array has probes targeting both strands of the genomic DNA in interested regions. Any suitable second strand cDNA synthesis inhibition methods are suitable for use with at least some embodiments of the invention. In particularly preferred embodiments, hairpin loop formation inhibition is used to inhibit second strand cDNA synthesis. In one particularly preferred embodiment, the synthesis of the second strand cDNA is inhibited by the presence of actinomycin D. The cDNAs or nucleic acids derived from the cDNAs (e.g., products of PCR amplification of the cDNAs, etc.) may be labeled with any suitable labels, such as radioactive labels, fluorescent labels, and chemoluminescent labels, etc. The nucleic acid array can be a high density oligonucleotide probe array with at least 400, 1000, 10000 probes per $cm^2$. In preferred embodiments, the array contains at least one probe against a target sequence and one probe against the reverse complementary sequence of the target sequence. In more preferred embodiments, the array contains at least 100 probes against at least 100 target sequences and at least 100 probes against at least 100 reverse complementary sequences of the target sequences. In even more preferred embodiments, the array comprises at least 1000 or 3000 probes against at least 1000 or 3000 target sequences and at least 1000 or 3000 probes against at least 1000 or 3000 reverse complementary sequences of the target sequences.

In yet another aspect of the invention, an assay kit is provided. The kit contains reagents necessary for a reverse transcription reaction; an inhibitor of second strand cDNA synthesis; and a nucleic acid probe array. In preferred embodiments, the inhibitor is actinomycin D. The nucleic acid probe array is an oligonucleotide probe array that has at least 400, 1000, 10000 probes per $cm^2$.

BRIEF DESCRIPTION OF DRAWINGS

The accompanying drawings, which are incorporated in and form a part of this specification, illustrate embodiments of the invention and, together with the description, serve to explain the principles of the invention.

DETAILED DESCRIPTION

Figure 1:
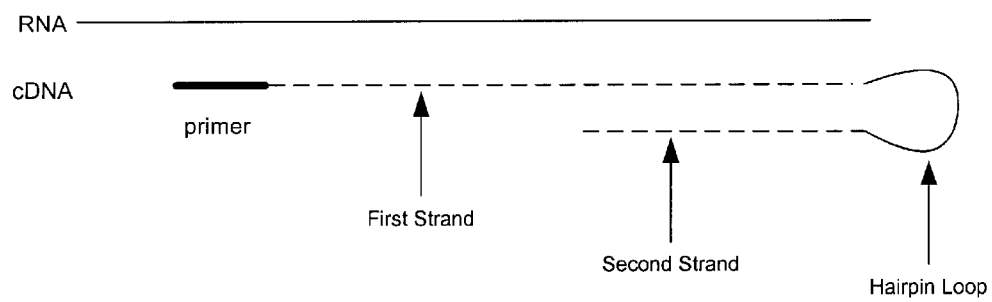
FIG. 1 is a schematic showing the role of hairpin loop in cDNA synthesis.

Reference will now be made in detail to the preferred embodiments of the invention. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention.

General

The present invention relies on many patents, applications and other references for certain details well known to those of the art. Therefore, when a patent, application, or other reference is cited or repeated below, it should be understood it is incorporated by reference in its entirety for all purposes as well as for the proposition that is recited.

As used in the specification and claims, the singular form a, an, and the include plural references unless the context clearly dictates otherwise. For example, the term an agent" includes a plurality of agents, including mixtures thereof.

An individual is not limited to a human being but may also be other organisms including but not limited to mammals, plants, bacteria, or cells derived from any of the above.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The practice of the present invention may employ, unless otherwise indicated, conventional techniques of organic chemistry, polymer technology, molecular biology (including recombinant techniques), cell biology, biochemistry, and immunology, which are within the skill of the art. Such conventional techniques include polymer array synthesis, hybridization, ligation, detection of hybridization using a label. Such conventional techniques can be found in standard laboratory manuals such as *Genome Analysis: A Laboratory Manual Series (Vols. I–IV), Using Antibodies: A Laboratory Manual, Cells: A Laboratory Manual, PCR Primer. A Laboratory Manual, and Molecular Cloning: A Laboratory Manual* (all from Cold Spring Harbor Laboratory Press), all of which are herein incorporated in their entirety by reference for all purposes.

Additional methods and techniques applicable to array synthesis have been described in U.S. Pat. Nos. 5,143,854, 5,242,974, 5,252,743, 5,324,633, 5,384,261, 5,405,783, 5,412,087, 5,424,186, 5,445,934, 5,451,683, 5,482,867, 5,489,678, 5,491,074, 5,510,270, 5,527,681, 5,550,215, 5,571,639, 5,578,832, 5,593,839, 5,599,695, 5,624,711, 5,631,734, 5,677,195, 5,744,101, 5,744,305, 5,770,456, 5,795,716, 5,800,992, 5,831,070, 5,837,832, 5,856,101, 5,871,928, 5,858,659, 5,936,324, 5,968,740, 5,974,164, 5,981,185, 5,981,956, 6,025,601, 6,033,860, 6,040,138, and 6,090,555, which are all incorporated herein by reference in their entirety for all purposes.

Analogue when used in conjunction with a biomonomer or a biopolymer refers to natural and un-natural variants of the particular biomonomer or biopolymer. For example, a nucleotide analogue includes inosine and dideoxynucleotides. A nucleic acid analogue includes peptide nucleic acids. The foregoing is not intended to be exhaustive but rather representative. More information can be found in U.S. patent application Ser. No. 80/630,427.

Complementary or substantially complementary: Refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementarity exists when an RNA or DNA strand will hybridize under selective hybridization conditions to its complement. Typically, selective hybridization will occur when there is at least about 65% complementarity over a stretch of at least 14 to 25 nucleotides, preferably at least about 75%, more preferably at least about 90% complementarity. See e. g., M. Kanehisa Nucleic Acids Res. 12:203 (1984), incorporated herein by reference.

Hybridization refers to the process in which two single-stranded polynucleotides bind non-covalently to form a stable double-stranded polynucleotide; triple-stranded hybridization is also theoretically possible. The resulting (usually) double-stranded polynucleotide is a hybrid. The proportion of the population of polynucleotides that forms stable hybrids is referred to herein as the degree of hybridization. Hybridizations are usually performed under stringent conditions, for example, at a concentration of no more than 1 M and a temperature of at least 25 E C. For example, conditions of 5×SSPE (750 NaCl, 50 NaPhosphate, 5 EDTA, pH 7.4) and a temperature of 25–30° C. are suitable for allele-specific probe hybridizations. For stringent conditions, see, for example, Sambrook, Fritsche and Maniatis. Molecular Cloning A laboratory Manual $2^{nd}$ Ed. Cold Spring Harbor Press (1989) which is hereby incorporated by reference in its entirety for all purposes above.

Nucleic acid refers to a polymeric form of nucleotides of any length, such as oligonucleotides or polynucleotides, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be customized to stabilize or destabilize hybrid formation or enhance the specificity of hybridization with a complementary nucleic acid sequence as desired.

Oligonucleotide or polynucleotide is a nucleic acid ranging from at least 2, preferable at least 8, and more preferably at least 20 nucleotides in length or a compound that specifically hybridizes to a polynucleotide. Polynucleotides of the present invention include sequences of deoxyribonucleic acid (DNA) or ribonucleic acid (RNA) or mimetics thereof which may be isolated from natural sources, recombinantly produced or artificially synthesized. A further example of a polynucleotide of the present invention may be a peptide nucleic acid (PNA). The invention also encompasses situations in which there is a nontraditional base pairing such as Hoogsteen base pairing which has been identified in certain tRNA molecules and postulated to exist in a triple helix. Polynucleotide and oligonucleotide are used interchangeably in this application.

Polymorphism refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms.

Primer is a single-stranded oligonucleotide capable of acting as a point of initiation for template-directed DNA synthesis under suitable conditions, e.g., buffer and temperature, in the presence of four different nucleoside triphosphates and an agent for polymerization, such as, for example, DNA or RNA polymerase or reverse transcriptase. The length of the primer, in any given case, depends on, for example, the intended use of the primer, and generally ranges from 3 to 6 and up to 30 or 50 nucleotides. Short primer molecules generally require cooler temperatures to form sufficiently stable hybrid complexes with the template. A primer need not reflect the exact sequence of the template but must be sufficiently complementary to hybridize with such template. The primer site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified.

Substrate refers to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations.

High density nucleic acid probe arrays, also referred to as DNA Microarrays, have become a method of choice for monitoring the expression of a large number of genes.

A target molecule refers to a biological molecule of interest. The biological molecule of interest can be a ligand, receptor, peptide, nucleic acid (oligonucleotide or polynucleotide of RNA or DNA), or any other of the biological molecules listed in U.S. Pat. No. 5,445,934 at col. 5, line 66 to col. 7, line 51. For example, if transcripts of genes are the interest of an experiment, the target molecules would be the transcripts. Other examples include protein fragments, small molecules, etc. Target nucleic acid refers to a nucleic acid (often derived from a biological sample) of interest. Frequently, a target molecule is detected using one or more probes. As used herein, a probe is a molecule for detecting a target molecule. It can be any of the molecules in the same classes as the target referred to above. A probe may refer to a nucleic acid, such as an oligonucleotide, capable of binding to a target nucleic acid of complementary sequence through one or more types of chemical bonds, usually through complementary base pairing, usually through hydrogen bond formation. As used herein, a probe may include natural (i.e. A, G, U, C, or T) or modified bases (7-deazaguanosine, inosine, etc.). In addition, the bases in probes may be joined by a linkage other than a phosphodiester bond, so long as the bond does not interfere with hybridization. Thus, probes may be peptide nucleic acids in which the constituent bases are joined by peptide bonds rather than phosphodiester linkages. Other examples of probes include antibodies used to detect peptides or other molecules, any ligands for detecting its binding partners. When referring to targets or probes as nucleic acids, it should be understood that there are illustrative embodiments that are not to limit the invention in any way.

In preferred embodiments, probes may be immobilized on substrates to create an array. An array may comprise a solid support with peptide or nucleic acid or other molecular probes attached to the support. Arrays typically comprise a plurality of different nucleic acids or peptide probes that are coupled to a surface of a substrate different, known locations. These arrays, also described as "microarrays" or colloquially "chips" have been generally described in the art, for example, in Fodor et al., Science, 251:767–777 (1991), which is incorporated by reference for all purposes. Methods of forming high density arrays of oligonucleotides, peptides and other polymer sequences with a minimal number of synthetic steps are disclosed in, for example, U.S. Pat. Nos. 5,143,854, 5,252,743, 5,384,261, 5,405,783, 5,424,186, 5,429,807, 5,445,943, 5,510,270, 5,677,195, 5,571,639, 6,040,138, all incorporated herein by reference for all purposes. The oligonucleotide analogue array can be synthesized on a solid substrate by a variety of methods, including, but not limited to, light-directed chemical coupling, and mechanically directed coupling. See Pirrung et al., U.S. Pat. No. 5,143,854 (see also PCT Application No. WO 90/15070) and Fodor et al., PCT Publication Nos. WO 92/10092 and WO 93/09668, U.S. Pat. Nos. 5,677,195, 5,800,992 and 6,156,501 which disclose methods of forming vast arrays of peptides, oligonucleotides and other molecules using, for example, light-directed synthesis techniques. See also, Fodor et al., Science, 251, 767–77 (1991). These procedures for synthesis of polymer arrays are now referred to as VLSIPS™ procedures. Using the VLSIPS™ approach, one heterogeneous array of polymers is converted, through simultaneous coupling at a number of reaction sites, into a different heterogeneous array. See, U.S. Pat. Nos. 5,384,261 and 5,677,195.

Methods for making and using molecular probe arrays, particularly nucleic acid probe arrays are also disclosed in, for example, U.S. Pat. Nos. 5,143,854, 5,242,974, 5,252,743, 5,324,633, 5,384,261, 5,405,783, 5,409,810, 5,412,087, 5,424,186, 5,429,807, 5,445,934, 5,451,683, 5,482,867, 5,489,678, 5,491,074, 5,510,270, 5,527,681, 5,527,681, 5,541,061, 5,550,215, 5,554,501, 5,556,752, 5,556,961, 5,571,639, 5,583,211, 5,593,839, 5,599,695, 5,607,832, 5,624,711, 5,677,195, 5,744,101, 5,744,305, 5,753,788, 5,770,456, 5,770,722, 5,831,070, 5,856,101, 5,885,837, 5,889,165, 5,919,523, 5,922,591, 5,925,517, 5,658,734, 6,022,963, 6,150,147, 6,147,205, 6,153,743, 6,140,044 and D430024, all of which are incorporated by reference in their entireties for all purposes.

Methods for signal detection and processing of intensity data are additionally disclosed in, for example, U.S. Pat. Nos. 5,547,839, 5,578,832, 5,631,734, 5,800,992, 5,856,092, 5,936,324, 5,981,956, 6,025,601, 6,090,555, 6,141,096, 6,141,096, and 5,902,723. Methods for array based assays, computer software for data analysis and applications are additionally disclosed in, e.g., U.S. Pat. Nos. 5,527,670, 5,527,676, 5,545,531, 5,622,829, 5,631,128, 5,639,423, 5,646,039, 5,650,268, 5,654,155, 5,674,742, 5,710,000, 5,733,729, 5,795,716, 5,814,450, 5,821,328, 5,824,477, 5,834,252, 5,834,758, 5,837,832, 5,843,655, 5,856,086, 5,856,104, 5,856,174, 5,858,659, 5,861,242, 5,869,244, 5,871,928, 5,874,219, 5,902,723, 5,925,525, 5,928,905, 5,935,793, 5,945,334, 5,959,098, 5,968,730, 5,968,740, 5,974,164, 5,981,174, 5,981,185, 5,985,651, 6,013,440, 6,013,449, 6,020,135, 6,027,880, 6,027,894, 6,033,850, 6,033,860, 6,037,124, 6,040,138, 6,040,193, 6,043,080, 6,045,996, 6,050,719, 6,066,454, 6,083,697, 6,114,116, 6,114,122, 6,121,048, 6,124,102, 6,130,046, 6,132,580, 6,132,996, 6,136,269 and U.S. patent application Ser. Nos. 09/735,743 and 09/737,536, all of which are incorporated by reference in their entireties for all purposes.

The embodiments of the invention will be described using GeneChip® high oligonucleotide density probe arrays (available from Affymetrix, Inc., Santa Clara, Calif., USA) as exemplary embodiments. One of skill in the art would appreciate that the embodiments of the invention are not limited to high density oligonucleotide probe arrays. In contrast, the embodiments of the invention are useful for analyzing any parallel large scale biological analysis, such as those using nucleic acid probe arrays, protein arrays, etc.

Gene expression monitoring using GeneChip® high density oligonucleotide probe arrays are described in, for example, Lockhart et al., 1996, Expression Monitoring By Hybridization to High Density Oligonucleotide Arrays, Nature Biotechnology 14:1675–1680; U.S. Pat. Nos. 6,040,138 and 5,800,992, all incorporated herein by reference in their entireties for all purposes.

Detection of Sense and Antisense Transcripts

Transcription entails the synthesis of a single-stranded polynucleotide of RNA at an unwound section of DNA with one of the DNA strands serving as a template for the synthesis of the RNA. The product of this process is called an RNA transcript. RNAs can be transcribed from either stand or both stands of the genomic DNA. In some instances, both strands of the same genomic DNA region may be transcribed. The term "template strand," as used herein, refers to the genomic DNA strand used as a template for a RNA transcript. The reverse complementary strand of the template strand is referred to as reverse strand. Because both strands can be used as templates, the terms "template strand" and "reverse strand, " as used herein, are often relative to particular transcripts.

As used herein, the term "sense strand" refers to the genomic DNA strand which is identical in sequence to the RNA transcribed. The actual template (template strand) for the transcription is the reverse strand of the sense strand. An antisense strand is the template strand for the transcript.

It is well known that both the sense and antisense transcripts of certain genes may encode proteins or regulate gene activities. One example of the sense and antisense transcription is the gene for neurofibromin, a tumor suppressor protein that is absent or inactivated in neurofibromatosis type 1 (NF1), an inherited illness that causes 'cafe-au-lait' spots on the skin and tumors beneath the skin. Within an intron of the neurofibromin gene, but encoded on the antisense strand of the DNA, are codons for three other proteins: oligodendrocyte-myelin glycoprotein which may control cell proliferation and two homologs of a mouse gene that causes myeloid leukemia.

Figure 2:
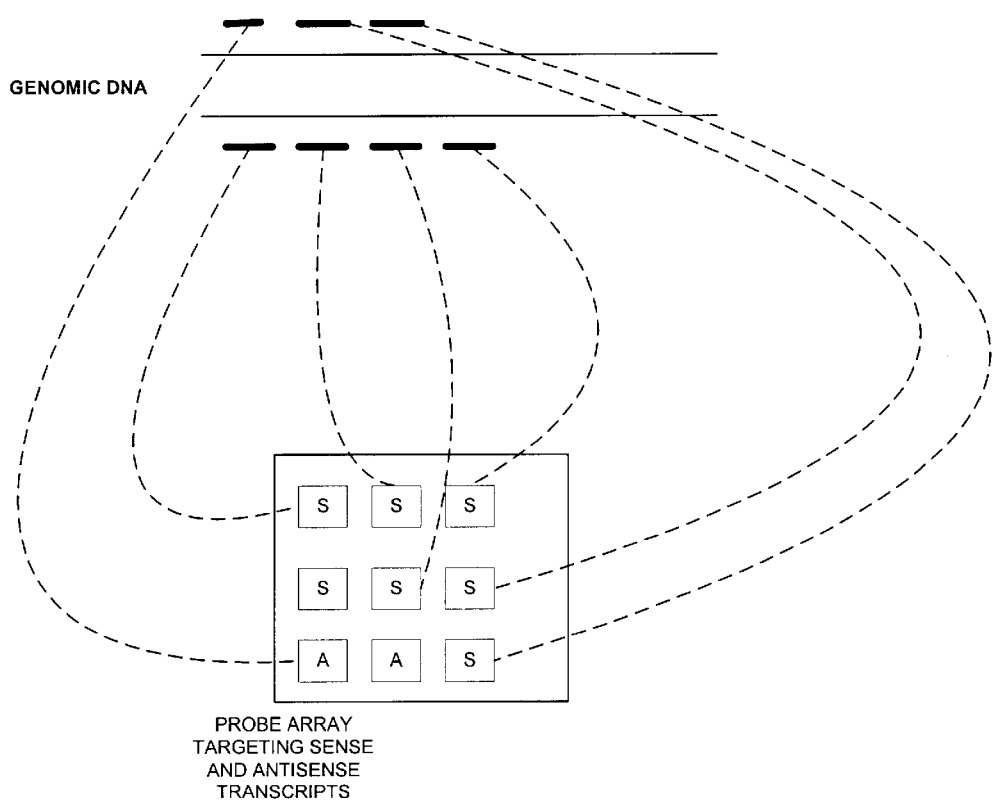
FIG. 2 is a schematic showing a probe array containing probes against both potential transcripts from both strand of the genomic DNA.

Nucleic acid probe arrays have been used to monitor a large number of transcripts simultaneously and are also being used to interrogate the genome for potential transcripts. In many instances, probes against both the sense and antisense transcripts or potential transcripts are detected simultaneously. Some of these applications use random hexamer or nanomer, or specific primers for cDNA synthesis for target preparation. As FIG. 1 shows, in addition to first strand cDNA synthesis, a second strand cDNA may be synthesized as well, using the hairpin loop as the primer. The second strand cDNA synthesis could make the data analysis complicated due to the additional strand synthesis, particularly if a probe array contains probes against both the sense and antisense transcript (see, FIG. 2). For example, in a case where the sense strand transcript, but not the antisense transcript, is present in a sample, a probe array against the antisense transcript may detect the second strand synthesized. Both the sense and antisense probes may show signals. Similarly, if the transcript present in the sample is an antisense transcript, the probes targeting both the sense and antisense transcripts may show signals, which could complicate data analysis.

The inventors have experimentally shown that second strand cDNA synthesis is mostly triggered by the hairpin loop formation at the 5' end of first-strand cDNA and not through repriming of cDNA with random hexamer primers. In one aspect of the invention, methods are provided for inhibiting the synthesis of the second strand cDNA synthesis and to improve the detection of sense and antisense transcripts, particularly when probes targeting sense and antisense transcripts are used simultaneously. The methods are particularly useful for interrogating the genome for potential transcripts. In such cases, because both strands of the genomic DNA can be used as templates, probes against potential transcripts from both strands are often used to determine potentially transcribed regions. In some embodiments of the invention, methods are provided to determine the template strand of the potential transcripts. The methods include preparing cDNAs from a transcript sample while the hairpin formation or second strand cDNA synthesis is inhibited. The cDNAs or nucleic acids are hybridized to a nucleic acid probe array. The array may contain probes against both strands of the genomic DNA. The hybridization data are used to analyze not only which region of the genome is transcribed, but also which strand of the genomic DNA is used as a template for a detected transcript.

Methods are also provided for detecting the expression of genes that have both sense and antisense transcripts. In such methods, probes against both the sense and antisense transcripts are used simultaneously. The signals from the sense and antisense probes are used to determine the relative level of the sense and antisense transcripts. If the second strand cDNA synthesis is not inhibited, both the sense and antisense probes may detect either sense or antisense transcripts, which makes data interpretation much more complicated.

The methods have applications in areas such as drug discovery and diagnostics. For example, new transcripts detected may serve as potential drug targets.

One of skill in the art would appreciate that any means for inhibiting the hairpin loop formation or the second strand cDNA synthesis can be used for some embodiments of the invention. In a particularly preferred embodiment, anti-tumor antibiotic, actinomycin D (AMD), is used to inhibit the hairpin formation and experiments have shown that actinomycin reduced the number of second strand cDNA transcripts by more than 64%. In some other embodiments, the addition of sodium pyrophosphate to the first strand cDNA synthesis is used to suppress hairpin formation. In additional embodiments, DMSO of appropriate concentration (such as 15% DMSO) can be used to suppress second strand synthesis with no apparent decrease in first strand synthesis (Gross, L. et. al. (1992) J. Mol. Biol. 228, 488, incorporated herein by reference).

In one aspect of the invention, methods are provided for detecting a plurality of transcripts without the interference of second strand DNA. The methods include synthesizing a plurality of cDNAs complementary with the transcripts by reverse transcription; where the synthesis of second strand cDNA is inhibited; and hybridizing the cDNAs or nucleic acids derived from the cDNAs with a nucleic acid probe array to detect the transcripts. The methods are particularly suitable for detecting a large number of, at least 100, 1000, or 10000, transcripts. Any suitable second strand cDNA synthesis inhibition methods are suitable for use with at least some embodiments of the invention. In particularly preferred embodiments, hairpin loop formation inhibition is used to inhibit second strand cDNA synthesis. In one particularly preferred embodiment, the synthesis of the second strand cDNA is inhibited by the presence of actinomycin D, DMSO or sodium pyrophosphate. The cDNAs or nucleic acids derived from the cDNAs (e.g., products of PCR amplification of the cDNAs, etc.) may be labeled with any suitable labels, such as radioactive labels, fluorescent labels, and chemoluminescent labels, etc.

The nucleic acid array can be a high density oligonucleotide probe array with at least 400, 1000, 10000 probes per $cm^2$. In preferred embodiments, the array contains at least one probe against a target sequence and one probe against the reverse complementary sequence of the target sequence. In more preferred embodiments, the array contains at least 100 probes against at least 100 target sequences and at least 100 probes against at least 100 reverse complementary sequences of the target sequences. In even more preferred embodiments, the array comprises at least 1000 or 3000 probes against at least 1000 or 3000 target sequences and at least 1000 or 3000 probes against at least 1000 or 3000 reverse complementary sequences of the target sequences.

In another aspect of the invention, methods are provided for detecting the transcribed regions of a genome. The methods are particularly suitable for analyzing regions where both strands of the genomic DNA are transcribed. In preferred embodiments, the methods include obtaining a sample containing transcripts transcribed from the genome; synthesizing single stranded cDNAs complementary with the transcripts, where the synthesis of second strand cDNA is inhibited; and hybridizing the cDNAs or nucleic acids derived from the cDNAs with a nucleic acid probe array, where the nucleic acid probe array has probes targeting both strands of the genomic DNA in interested regions.

Any suitable second strand cDNA synthesis inhibition methods are suitable for use with at least some embodiments of the invention. In particularly preferred embodiments, hairpin loop formation inhibition is used to inhibit second strand cDNA synthesis. In one particularly preferred embodiment, the synthesis of the second strand cDNA is inhibited by the presence of actinomycin D. The cDNAs or nucleic acids derived from the cDNAs (e.g., products of PCR amplification of the cDNAs, etc.) may be labeled with any suitable labels, such as radioactive labels, fluorescent labels, and chemoluminescent labels, etc.

The nucleic acid array can be a high density oligonucleotide probe array with at least 400, 1000, 10000 probes per $cm^2$. In preferred embodiments, the array contains at least one probe against a target sequence and one probe against the reverse complementary sequence of the target sequence. In more preferred embodiments, the array contains at least 100 probes against at least 100 target sequences and at least 100 probes against at least 100 reverse complementary sequences of the target sequences. In even more preferred embodiments, the array comprises at least 1000 or 3000 probes against at least 1000 or 3000 target sequences and at least 1000 or 3000 probes against at least 1000 or 3000 reverse complementary sequences of the target sequences.

In yet another aspect of the invention, an assay kit is provided. The kit contains reagents necessary for a reverse transcription reaction; an inhibitor of second strand cDNA synthesis; and a nucleic acid probe array. In preferred embodiments, the inhibitor is actinomycin D. The nucleic acid probe array is an oligonucleotide probe array that has at least 400, 1000, 10000 probes per $cm^2$.

Sample Preparation and Hybridization

The methods of the invention are not limited to any particular method of sample preparation. A large number of well-known methods for isolating and purifying RNA are suitable for this invention.

One of skill in the art will appreciate that it is desirable to have nucleic acid samples containing target nucleic acid sequences that reflect the transcripts of interest. Therefore, suitable nucleic acid samples may contain transcripts of interest. Suitable nucleic acid samples, however, may also contain nucleic acids derived from the transcripts of interest. As used herein, a nucleic acid derived from a transcript refers to a nucleic acid for whose synthesis the mRNA transcript or a subsequence thereof has ultimately served as a template. Thus, a cDNA reverse transcribed from a transcript, an RNA transcribed from that cDNA, a DNA amplified from the cDNA, an RNA transcribed from the amplified DNA, etc., are all derived from the transcript and detection of such derived products is indicative of the presence and/or abundance of the original transcript in a sample. Thus, suitable samples include, but are not limited to, transcripts of the gene or genes, cDNA reverse transcribed from the transcript, cRNA transcribed from the cDNA, DNA amplified from the genes, RNA transcribed from amplified DNA, and the like. Transcripts, as used herein, may include, but are not limited to pre-mRNA nascent transcript(s), transcript processing intermediates, mature mRNA(s) and degradation products. It is not necessary to monitor all types of transcripts to practice this invention. For example, one may choose to practice the invention to measure the mature mRNA levels only.

In one embodiment, such a sample is a homogenate of cells or tissues or other biological samples. Preferably, such sample is a total RNA preparation of a biological sample. More preferably in some embodiments, such a nucleic acid sample is the total mRNA isolated from a biological sample. Those of skill in the art will appreciate that the total mRNA prepared with most methods includes not only the mature mRNA, but also the RNA processing intermediates and nascent pre-mRNA transcripts. For example, total mRNA purified with poly (T) column contains RNA molecules with poly (A) tails. Those poly A+ RNA molecules could be mature mRNA, RNA processing intermediates, nascent transcripts or degradation intermediates.

Biological samples may be of any biological tissue or fluid or cells. Frequently the sample will be a "clinical sample" which is a sample derived from a patient. Clinical samples provide a rich source of information regarding the various states of genetic network or gene expression. Some embodiments of the invention are employed to detect mutations and to identify the function of mutations. Such embodiments have extensive applications in clinical diagnostics and clinical studies. Typical clinical samples include, but are not limited to, sputum, blood, blood cells (e.g., white cells), tissue or fine needle biopsy samples, urine, peritoneal fluid, and pleural fluid, or cells therefrom. Biological samples may also include sections of tissues such as frozen sections taken for histological purposes.

Another typical source of biological samples are cell cultures where gene expression states can be manipulated to explore the relationship among genes. In one aspect of the invention, methods are provided to generate biological samples reflecting a wide variety of states of the genetic network.

One of skill in the art would appreciate that it is desirable to inhibit or destroy RNase present in homogenates before homogenates can be used for hybridization. Methods of inhibiting or destroying nucleases are well known in the art. In some preferred embodiments, cells or tissues are homogenized in the presence of chaotropic agents to inhibit nuclease. In some other embodiments, RNase are inhibited or destroyed by heat treatment followed by proteinase treatment.

Methods of isolating total RNA and mRNA are also well known to those of skill in the art. For example, methods of isolation and purification of nucleic acids are described in detail in Chapter 3 of Laboratory Techniques in Biochemistry and Molecular Biology: Hybridization With Nucleic Acid Probes, Part I. Theory and Nucleic Acid Preparation, P. Tijssen, ed. Elsevier, N.Y. (1993) and Chapter 3 of Laboratory Techniques in Biochemistry and Molecular Biology: Hybridization With Nucleic Acid Probes, Part I. Theory and Nucleic Acid Preparation, P. Tijssen, ed. Elsevier, N.Y. (1993)).

In a preferred embodiment, the total RNA is isolated from a given sample using, for example, an acid guanidinium-phenol-chloroform extraction method and polyA+ mRNA is isolated by oligo (dT) column chromatography or by using (dT) magnetic beads (see, e.g., Sambrook et al., Molecular Cloning: A Laboratory Manual (2nd ed.), Vols.1–3, Cold Spring Harbor Laboratory, (1989), or Current Protocols in Molecular Biology, F. Ausubel et al., ed. Greene Publishing and Wiley-lnterscience, New York (1987)).

Most of eukaroytic mRNA have 3" poly (A) tails, some of eukaroytic and all of prokaroytic mRNA do not contain 3" poly (A) tails. It is often desirable to isolate mRNAs from RNA samples.

In one particularly preferred embodiment, total RNA is isolated from mammalian cells using RNeasy Total RNA isolation kit (QIAGEN). If mammalian tissue is used as the source of RNA, a commercial reagent such as TRIzol Reagent (GIBCOL Life Technologies) may be used. A second cleanup after the ethanol precipitation step in the TRIzol extraction using Rneasy total RNA isolation kit may be beneficial.

Hot phenol protocol described by Schmitt, et al., (1990) Nucleic Acid Res., 18:3091–3092 is useful for isolating total RNA for yeast cells.

Good quality mRNA may be obtained by, for example, first isolating total RNA and then isolating the mRNA from the total RNA using Oligotex mRNA kit (QIAGEN).

Total RNA from prokaryotes, such as $E.\ coli$ cells, may be obtained by following the protocol for MasterPure complete DNA/RNA purification kit from Epicentre Technologies (Madison, Wis.).

Frequently, it is desirable to amplify the nucleic acid sample prior to hybridization. One of skill in the art will appreciate that whatever amplification method is used, if a quantitative result is desired, care must be taken to use a method that maintains or controls for the relative frequencies of the amplified nucleic acids to achieve quantitative amplification.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. The high density array may then include probes specific to the internal standard for quantification of the amplified nucleic acid.

Other suitable amplification methods include, but are not limited to polymerase chain reaction (PCR) (Innis, et al., PCR Protocols. A guide to Methods and Application. Academic Press, Inc. San Diego, (1990)), ligase chain reaction (LCR) (see Wu and Wallace, Genomics, 4: 560 (1989), Landegren, et al., Science, 241: 1077 (1988) and Barringer, et al., Gene, 89: 117 (1990), transcription amplification (Kwoh, et al., Proc. Natl. Acad. Sci. USA, 86: 1173 (1989)), and self-sustained sequence replication (Guatelli, et al., Proc. Nat. Acad. Sci. USA, 87: 1874 (1990)).

Cell lysates or tissue homogenates often contain a number of inhibitors of polymerase activity. Therefore, RT-PCR typically incorporates preliminary steps to isolate total RNA or mRNA for subsequent use as an amplification template. One tube mRNA capture method may be used to prepare poly(A)+ RNA samples suitable for immediate RT-PCR in the same tube (Boehringer Mannheim). The captured mRNA can be directly subjected to RT-PCR by adding a reverse transcription mix and, subsequently, a PCR mix.

In a particularly preferred embodiment, the sample mRNA is reverse transcribed with a reverse transcriptase and a primer consisting of oligo dT, random hexamer, random nanomer or other primers, to provide a single stranded DNA template. The reverse transcription reactions are preferably performed in a condition that suppresses the hairpin formation to reduce second strand cDNA synthesis. For example, actinomycin D (Actinomycin D with mannitol (Sigma) was dissolved in water to a stock concentration of 1 mg/ml.) may be added before the reverse transcription reaction is initiated. One of skill in the art would appreciate that the scope of the invention is not limited to the particular concentration described herein. It is well within the skill of one of ordinary skills in the art to optimize assays by varying the concentration of reagents according to the need of the particular experimental purpose and experimental conditions.

Before hybridization, the resulting cRNA or cDNA may be fragmented. One preferred method for fragmentation employs Rnase free RNA fragmentation buffer (200 mM tris-acetate, pH 8.1, 500 mM potassium acetate, 150 mM magnesium acetate). Approximately 20 μg of cRNA is mixed with 8 μL of the fragmentation buffer. Rnase free water is added to make the volume to 40 μL. The mixture may be incubated at 94° C. for 35 minutes and chilled in ice.

The biological sample should contain nucleic acids that reflects the level of at least some of the transcripts present in the cell, tissue or organ of the species of interest. In some embodiments, the biological sample may be prepared from cells, tissues or organs of a particular status, for example, a total RNA preparation from the pituitary of a dog when the dog is pregnant. In another example, samples may be prepared from E. coli cells after the cells are treated with IPTG. Because certain genes may only be expressed under certain conditions, biological samples derived under various conditions may be needed to observe all transcripts. In some instances, the transcriptional annotation may be specific for a particular physiological, pharmacological or toxicological condition. For example, certain regions of a gene may only be transcribed under specific physiological conditions. Transcript annotation obtained using biological samples from the specific physiological conditions may not be applicable to other physiological conditions.

Nucleic acid hybridization simply involves contacting a probe and target nucleic acid under conditions where the probe and its complementary target can form stable hybrid duplexes through complementary base pairing.

It is generally recognized that nucleic acids are denatured by increasing the temperature or decreasing the salt concentration of the buffer containing the nucleic acids. Under low stringency conditions (e.g., low temperature and/or high salt) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

One of skill in the art will appreciate that hybridization conditions may be selected to provide any degree of stringency. In a preferred embodiment, hybridization is performed at low stringency in this case in 6×SSPE-T at 37 C. (0.005% Triton X-100) to ensure hybridization and then subsequent washes are performed at higher stringency (e.g., 1×SSPE-T at 37 C.) to eliminate mismatched hybrid duplexes. Successive washes may be performed at increasingly higher stringency (e.g., down to as low as 0.25× SSPE-T at 37 C. to 50 C.) until a desired level of hybridization specificity is obtained. Stringency can also be increased by addition of agents such as formamide. Hybridization specificity may be evaluated by comparison of hybridization to the test probes with hybridization to the various controls that can be present (e.g., expression level control, normalization control, mismatch controls, etc.).

In general, there is a tradeoff between hybridization specificity (stringency) and signal intensity. Thus, in a preferred embodiment, the wash is performed at the highest stringency that produces consistent results and that provides a signal intensity greater than approximately 10% of the background intensity. Thus, in a preferred embodiment, the hybridized array may be washed at successively higher stringency solutions and read between each wash. Analysis of the data sets thus produced will reveal a wash stringency above which the hybridization pattern is not appreciably altered and which provides adequate signal for the particular oligonucleotide probes of interest.

Altering the thermal stability (Tm) of the duplex formed between the target and the probe using, e.g., known oligonucleotide analogues allows for optimization of duplex stability and mismatch discrimination. One useful aspect of altering the Tm arises from the fact that adenine-thymine (A-T) duplexes have a lower Tm than guanine-cytosine (G-C) duplexes, due in part to the fact that the A-T duplexes have 2 hydrogen bonds per base-pair, while the G-C duplexes have 3 hydrogen bonds per base pair. In heterogeneous oligonucleotide arrays in which there is a non-uniform distribution of bases, it is not generally possible to optimize hybridization for each oligonucleotide probe simultaneously. Thus, in some embodiments, it is desirable to selectively destabilize G-C duplexes and/or to increase the stability of A-T duplexes. This can be accomplished, e.g., by substituting guanine residues in the probes of an array which form G-C duplexes with hypoxanthine, or by substituting adenine residues in probes which form A-T duplexes with 2,6 diaminopurine or by using the salt tetramethyl ammonium chloride (TMACl) in place of NaCl.

Methods of optimizing hybridization conditions are well known to those of skill in the art (see, e.g., Laboratory Techniques in Biochemistry and Molecular Biology, Vol. 24: Hybridization With Nucleic Acid Probes, P. Tijssen, ed. Elsevier, N.Y., (1993)).

Signal Detection and Data Analysis

In a preferred embodiment, the hybridized nucleic acids are detected by detecting one or more labels attached to the sample nucleic acids. The labels may be incorporated by any of a number of means well known to those of skill in the art. However, in a preferred embodiment, the label is simultaneously incorporated during the amplification step in the preparation of the sample nucleic acids. Thus, for example, polymerase chain reaction (PCR) with labeled primers or labeled nucleotides will provide a labeled amplification product. In a preferred embodiment, transcription amplification, as described above, using a labeled nucleotide (e.g. fluorescein-labeled UTP and/or CTP) incorporates a label into the transcribed nucleic acids. Alternatively, cDNAs synthesized using a RNA sample as a template, cRNAs are synthesized using the cDNAs as templates using in vitro transcription (IVT). A biotin label may be incorporated during the IVT reaction (Enzo Bioarray high yield labeling kit).

Alternatively, a label may be added directly to the original nucleic acid sample (e.g., mRNA, polyA mRNA, cDNA, etc.) or to the amplification product after the amplification is completed. Means of attaching labels to nucleic acids are well known to those of skill in the art and include, for example nick translation or end-labeling (e.g. with a labeled RNA) by kinasing of the nucleic acid and subsequent attachment (ligation) of a nucleic acid linker joining the sample nucleic acid to a label (e.g., a fluorophore).

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., 3H, 125I, 35S, 14C, or 32P), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label. One particularly preferred method uses colloidal gold label that can be detected by measuring scattered light.

The label may be added to the target (sample) nucleic acid(s) prior to, or after the hybridization. So called "direct labels" are detectable labels that are directly attached to or incorporated into the target (sample) nucleic acid prior to hybridization. In contrast, so called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin bearing hybrid duplexes providing a label that is easily detected. For a detailed review of methods of labeling nucleic acids and detecting labeled hybridized nucleic acids see Laboratory Techniques in Biochemistry and Molecular Biology, Vol. 24: Hybridization With Nucleic Acid Probes, P. Tijssen, ed. Elsevier, N.Y., (1993).

Fluorescent labels are preferred and easily added during an in vitro transcription reaction. In a preferred embodiment, fluorescein labeled UTP and CTP are incorporated into the RNA produced in an in vitro transcription reaction as described above.

Means of detecting labeled target (sample) nucleic acids hybridized to the probes of the high density array are known to those of skill in the art. Thus, for example, where a colorimetric label is used, simple visualization of the label is sufficient. Where a radioactive labeled probe is used, detection of the radiation (e.g. with photographic film or a solid state detector) is sufficient.

In a preferred embodiment, however, the target nucleic acids are labeled with a fluorescent label and the localization of the label on the probe array is accomplished with fluorescent microscopy. The hybridized array is excited with a light source at the excitation wavelength of the particular fluorescent label and the resulting fluorescence at the emission wavelength is detected. In a particularly preferred embodiment, the excitation light source is a laser appropriate for the excitation of the fluorescent label.

The confocal microscope may be automated with a computer-controlled stage to automatically scan the entire high density array. Similarly, the microscope may be equipped with a phototransducer (e.g., a photomultiplier, a solid state array, a CCD camera, etc.) attached to an automated data acquisition system to automatically record the fluorescence signal produced by hybridization to each oligonucleotide probe on the array. Such automated systems are described at length in U.S. Pat. No: 5,143,854, PCT Application 20 92/10092, and U.S. application Ser. No. 08/195,889 filed on Feb. 10, 1994. Use of laser illumination in conjunction with automated confocal microscopy for signal detection permits detection at a resolution of better than about 100 $\mu$m, more preferably better than about 50 $\mu$m, and most preferably better than about 25 $\mu$m.

One of skill in the art will appreciate that methods for evaluating the hybridization results vary with the nature of the specific probe nucleic acids used as well as the controls provided. In the simplest embodiment, simple quantification of the fluorescence intensity for each probe is determined. This is accomplished simply by measuring probe signal strength at each location (representing a different probe) on the high density array (e.g., where the label is a fluorescent label, detection of the amount of florescence (intensity) produced by a fixed excitation illumination at each location on the array). Comparison of the absolute intensities of an array hybridized to nucleic acids from a "test" sample with intensities produced by a "control" sample provides a measure of the relative expression of the nucleic acids that hybridize to each of the probes.

One of skill in the art, however, will appreciate that hybridization signals will vary in strength with efficiency of hybridization, the amount of label on the sample nucleic acid and the amount of the particular nucleic acid in the sample. Typically nucleic acids present at very low levels (e.g., <1 pM) will show a very weak signal. At some low level of concentration, the signal becomes virtually indistinguishable from the background. In evaluating the hybridization data, a threshold intensity value may be selected below which a signal is not counted as being essentially indistinguishable from the background.

Suitable scanners, computer software for controlling the scanners and computer software for data management and analysis are available from commercial sources, such as Affymetrix, Inc., Santa Clara, Calif.

EXAMPLE

This example illustrates one embodiment of the invention.
Material and Methods
Bacterial growth conditions. A single colony of *E.coli* K-12 (MG1655) was inoculated in 5 ml of Luria-Bertani (LB) broth and grown overnight with constant aeration at 37° C. The next day 20 ml of LB broth was inoculated with 0.2 ml of the overnight culture and grown at 37° C. with constant aeration to an optical density ($OD_{600}$) of 0.8. The cells were incubated for 30 mm before RNA isolation.
RNA isolation. Total RNA was isolated from the cells using the protocol accompanying the MasterPure complete DNA/RNA purification kit from Epicentre Technologies (Madison, Wis). Isolated RNA was resuspended in diethylpyrocarbonate (DEPC)-treated water, quantitated based on absorption at 260 nm and stored in aliquots at −20° C. until further use.
mRNA enrichment and labeling. Enrichment of mRNA was done as described in the Affymetrix Expression Technical Manual (Affymetrix Inc., Santa Clara, Calif.). In brief, a set of oligonucleotide primers specific for either 16S or 23S rRNA are mixed with total RNA isolated from bacterial cultures. After annealing at 70° C. for 5 mm, 300 U MMLV reverse transcriptase (Epicentre Technologies, Madison, Wis.) is added to synthesize cDNA strands complementary to the two rRNA species. The cDNA strand synthesis allows for selective degradation of the 16S and 23S rRNAs by RNase H. Treatment of the RNA/cDNA mixture with DNase I (Amersham Pharmacia Biotech, Piscataway, N.J.) removes the cDNA molecules and oligonucleotide primers, which results in an RNA preparation that is enriched for mRNA by 80% (data not shown). For direct labeling of RNA, 20 $\mu$g enriched bacterial RNA was fragmented at 95° C. for 30 min in a total volume of 88 $\mu$l of 1× NEB buffer for T4 polynucleotide kinase (New England Biolabs, Beverly, Mass.). After cooling to 4° C., 50 $\mu$M -S-ATP (Roche Molecular Biochemicals, Indianapolis, Ind.) and 100 U T4 polynucleotide kinase (Roche Molecular Biochemicals) was added to the fragmented RNA and the reaction was incubated at 37° C. for 50 min. To inactivate T4 polynucleotide kinase, the reaction was incubated for 10 min at 65° C. and the RNA was subsequently ethanol precipitated to remove excess -S-ATP. After centrifugation the RNA pellet was resuspended in 96 μl of 30 mM MOPS, pH 7.5, and 4 μl of a 50 mM PEO-iodoacetylbiotin (Pierce Chemical, Rockford, Ill.) solution was added to introduce the biotin label. The reaction was incubated at 37° C. for 1 h and the labeled RNA was purified using the RNA/DNA Mini-Kit from Qiagen (Valencia, Calif.) as recommended by the manufacturer. Eluted RNA was quantitated based on the absorption at 260 nm and hybridized to the oligonucleotide array.

cDNA synthesis and labeling. For the cDNA synthesis method, 10 μg total RNA was reverse transcribed using the SuperScript II system for first strand cDNA synthesis from Life Technologies (Rockville, Md.). For the reaction, 500 ng random hexamers were mixed with the RNA in a total volume of 12 μl and heated to 70° C. for 10 min. After cooling to 25° C. within 10 min, the reaction buffer was added according to the manufacturer's recommendations. After increasing the temperature to 42° C. within 10 min, 1800 U SuperScript II was added to the reaction and incubated for 50 min. SuperScript II was heat inactivated at 72° C. for 15 min and the mixture cooled to 4° C. RNA was removed using 2 U RNase H (Life Technologies) and 1 μg RNase A (Epicentre, Madison, Wis.) for 10 min at 37° C. in 100 μl total volume. The cDNA was purified using the QiaQuick PCR purification kit from Qiagen (Valencia, Calif.). Isolated cDNA was quantitated based on the absorption at 260 nm and fragmented using a partial DNase I digest. For up to 5 μg isolated cDNA, 0.2 U DNase I (Roche Molecular Biochemicals) was added and incubated for 10 min at 37° C. in 1× One-Phor-All buffer (Amersham Pharmacia Biotech) and the reaction stopped by incubation at 99° C. for 10 min. The fragmentation was confirmed on a 0.7% agarose gel to verify that the fragments had an average length of 50–100 bp. The fragmented cDNA was 3'-end-labeled for 2 h at 37° C. using 175 U terminal transferase (Roche Molecular Biochemicals) and 70 μM biotin-N6-ddATP (DuPont/NEN, Boston, Mass.) in 1× TdT buffer (0.2 M potassium cacodylate, 25 mM Tris-HCl, 0.25 mg ml$^{-1}$ BSA, pH 6.6; Roche Molecular Biochemicals) and 2.5 mM cobalt chloride. The fragmented and end-labeled cDNA was added to the hybridization solution without further purification. In some experiments, actinomycin D with mannitol (Sigma) was dissolved in water to a stock concentration of 1 mg/ml. The absorbance at 440 nm was used to determine the final concentration of 50 ug/ml actionmycin D and was added to the reverse transcription reaction before addition of the Superscript II.

Oligonucleotide Probe Array. On the oligonucleotide arrays a given gene and Ig region is represented by 15 different 25mer oligonucleotides that are designed to be complementary to the target sequence and serve as unique, sequence-specific detectors (termed perfect match probes). An additional control element on these arrays is the use of mismatch (MM) control probes that are designed to be identical to their perfect match (PM) partners except for a single base difference in the central position. The presence of the MM oligonucleotide allows cross-hybridization and local background to be estimated and subtracted from the PM signal. For a given transcript the numbers of positive and negative probe pairs, as well as the PM and MM intensities, are used to determine whether a transcript is present (P), marginal (M) or absent (A). A probe pair is called positive when the intensity of the PM probe cell is significantly greater than that of the corresponding MM probe cell; a probe pair is called negative if the situation is reversed. The average difference (Avg Diff) of all 15 probes in a probe set is used to determine the level of expression of a transcript and is calculated by taking the difference between the PM and MM of every probe and averaging the differences over the entire probe set, with some trimming of outlier values.

Array hybridization and scanning. The hybridization solution contained 100 mM MES, 1 M NaCl, 20 mM EDTA and 0.01% Tween 20, pH 6.6 (referred to as 1× MES). In addition, the solution contained 0.1 mg/ml herring sperm DNA, 0.5 mg/ml BSA and 0.5 nM control Biotin-oligo 948. Samples were heated to 99° C. for 5 mm, followed by 45° C. for an additional 5 min before being placed in the array cartridge. Hybridization was carried out at 45° C. for 16 h with mixing on a rotary mixer at 60 r.p.m. Following hybridization, the sample solution was removed and the array was washed and stained as recommended in the technical manual (Affymetrix Inc.). In brief, to enhance the signals 10 μg/ml streptavidin and 2 mg/ml BSA in 1× MES was used as the first staining solution. After the streptavidin solution was removed, an antibody mix was added as the second stain, containing 0.1 mg/ml goat IgG, 5 μg/ml biotin-bound anti-streptavidin antibody and 2 mg/ml BSA in 1× MES. Nucleic acid was fluorescently labeled by incubation with 10 μg/ml streptavidin-phycoerythrin (Molecular Probes, Eugene, Oreg.) and 2 mg/ml BSA in 1× MES. The arrays were read at 570 nm with a resolution of 3 μm using a confocal laser scanner (Affymetrix Inc.).

Results

The addition of actinomycin D to the cDNA reaction did not significantly affect first-strand synthesis but significantly caused the number of present calls to decrease by 64% on the sense array, indicating second-strand inhibition (See, table 1). The remaining genes that were still present on the sense array were then studied. It was found that 67% of these genes were also present on the sense chip indicating an alternative mechanism for second strand cDNA synthesis or antisense transcripts. The other 32% were not present on the antisense arrays and are thought to be candidates for antisense RNAs. Our results allow reverse transcription to be studied on a global level, not only elucidating that the hairpin structure is the primary source of priming for second-strand cDNA, but also allowing the identification of potential antisense transcripts.

TABLE 1

Effect of Actinomycin D on Detection of Transcripts

| Array | Experiments | No. of Calls | Mean average difference of present calls. |
|---|---|---|---|
| Antisense | Actinomycin D | 2574 | 2300 |
| Antisense | No Actinomycin | 2396 | 2320 |
| Sense | Actinomycin D | 950 | 1100 |
| Sense | No Actinomycin | 432 | 1000 |

The present inventions provide methods for analyzing a large number of RNAs. It is to be understood that the above description is intended to be illustrative and not restrictive. Many variations of the invention will be apparent to those of skill in the art upon reviewing the above description. By way of example, the invention has been described primarily with reference to the use of a high density oligonucleotide array, but it will be readily recognized by those of skill in the art that other nucleic acid arrays are also within the scope of the invention. The scope of the invention should be determined with reference to the appended claims, along with the full scope of equivalents to which such claims are entitled. All cited references, including patent and non-patent literature, are incorporated herewith by reference in their entireties for all purposes.

What is claimed is:

1. A method for detecting a plurality of transcripts comprising:
   synthesizing a plurality of cDNAs complementary with the transcripts by reverse transcription; wherein the synthesis of second strand cDNA is inhibited; and
   hybridizing the cDNAs or nucleic acids derived from the cDNAs with a nucleic acid probe array to detect the transcripts.

2. The method of claim 1 wherein the synthesis of the second strand cDNA is inhibited by the presence of actinomycin.

3. The method of claim 2 wherein the cDNAs or nucleic acids derived from the cDNAs are labeled.

4. The method of claim 2 wherein the nucleic acid probe array is an oligonucleotide probe array.

5. The method of claim 4 wherein the nucleic acid probe array has at least 400 probes per $cm^2$.

6. The method of claim 5 wherein the nucleic acid probe array has at least 1000 probes per $cm^2$.

7. The method of claim 6 wherein the nucleic acid probe array has at least 10000 probes per $cm^2$.

8. A method for detecting transcribed regions of a genome comprising
   obtaining a sample comprising transcripts transcribed from the genome;
   synthesizing single stranded cDNAs complementary with the transcripts, wherein the synthesis of second strand cDNA is inhibited; and
   hybridizing the cDNAs or nucleic acids derived from the cDNAs with a nucleic acid probe array, wherein the nucleic acid probe array has probes targeting both strands of the genomic DNA in interested regions.

9. The method of claim 8 wherein the synthesis of the second strand cDNA is inhibited by the presence of actinomycin.

10. The method of claim 9 wherein the cDNAs or nucleic acids derived from cDNAs are labeled.

11. The method of claim 10 wherein the nucleic acid probe array is an oligonucleotide probe array.

12. The method of claim 11 wherein the nucleic acid probe array has at least 400 probes per $cm^2$.

13. The method of claim 12 wherein the nucleic acid probe array has at least 1000 probes per $cm^2$.

14. The method of claim 13 wherein the nucleic acid probe array has at least 10000 probes per $cm^2$.

15. The method of claim 8 further comprising determining the template strand for at least one transcript, and wherein the probe array contains probes against both strand of the genomic DNA region where the transcript is transcribed.

16. An assay kit comprising:
    reagents necessary for a reverse transcription reaction;
    an inhibitor of second strand cDNA synthesis; and
    a nucleic acid probe array.

17. The kit of claim 16 wherein the inhibitor is actinomycin D.

18. The kit of claim 17 wherein the nucleic acid probe array is an oligonucleotide probe array.

19. The kit of claim 18 wherein the nucleic acid probe array has at least 400 probes per $cm^2$.

20. The kit of claim 19 wherein the nucleic acid probe array has at least 1000 probes per $cm^2$.

21. The kit of claim 20 wherein the nucleic acid probe array has at least 10000 probes per $cm^2$.

22. The kit of claim 21 wherein the nucleic acid probe array comprises at least one probe against a target sequence and one probe against the reverse complementary sequence of the target sequence.

23. The kit of claim 22 wherein the nucleic acid probe array comprises at least 100 probes against at least 100 target sequences and at least 100 probes against at least 100 reverse complementary sequences of the target sequences.

24. The kit of claim 23 wherein the nucleic acid probe array comprises at least 1000 probes against at least 1000 target sequences and at least 1000 probes against at least 1000 reverse complementary sequences of the target sequences.

25. The kit of claim 24 wherein the nucleic acid probe array comprises at least 3000 probes against at least 3000 target sequences and at least 3000 probes against at least 3000 reverse complementary sequences of the target sequences.

* * * * *